United States Patent
Walters et al.

(10) Patent No.: US 7,604,636 B1
(45) Date of Patent: Oct. 20, 2009

(54) METHOD AND APPARATUS FOR ARTHROSCOPIC TUNNELING

(75) Inventors: Troy M Walters, Plymouth, IN (US); Kevin T Stone, Winona Lake, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 611 days.

(21) Appl. No.: 10/828,494

(22) Filed: Apr. 20, 2004

(51) Int. Cl.
*A61B 17/00* (2006.01)

(52) U.S. Cl. ...................................................... 606/80

(58) Field of Classification Search .................. 606/80, 606/86, 86 R, 104
See application file for complete search history.

(56) References Cited

U.S. PATENT DOCUMENTS

| | | | |
|---|---|---|---|
| 550,783 A | 12/1895 | Elliott et al. | |
| 4,265,231 A | 5/1981 | Scheller, Jr. et al. | |
| 4,345,601 A * | 8/1982 | Fukuda | 606/147 |
| 4,541,423 A | 9/1985 | Barber | |
| 4,872,451 A * | 10/1989 | Moore et al. | 606/72 |
| 4,941,466 A | 7/1990 | Romano | |
| 5,002,546 A * | 3/1991 | Romano | 606/80 |
| 5,017,057 A * | 5/1991 | Kryger | 408/68 |
| 5,395,188 A * | 3/1995 | Bailey et al. | 408/127 |
| 5,488,761 A | 2/1996 | Leone | |
| 5,509,918 A * | 4/1996 | Romano | 606/80 |
| 5,694,951 A | 12/1997 | Bonutti | |
| 5,700,265 A | 12/1997 | Romano | |
| 5,851,208 A | 12/1998 | Trott | |
| 6,053,922 A | 4/2000 | Krause et al. | |
| 6,267,679 B1 | 7/2001 | Romano | |
| 6,328,744 B1 * | 12/2001 | Harari et al. | 606/80 |
| 6,375,573 B2 | 4/2002 | Romano | |
| 6,447,518 B1 | 9/2002 | Krause et al. | |
| 6,468,289 B1 | 10/2002 | Bonutti | |
| 6,719,803 B2 * | 4/2004 | Bonutti | 623/23.63 |
| 6,740,090 B1 * | 5/2004 | Cragg et al. | 606/79 |
| 2002/0045903 A1 | 4/2002 | Bonutti | |
| 2002/0055755 A1 | 5/2002 | Bonutti | |
| 2002/0095214 A1 * | 7/2002 | Hyde, Jr. | 623/18.12 |
| 2004/0147934 A1 * | 7/2004 | Kiester | 606/80 |

OTHER PUBLICATIONS

"CurvTek Bone Tunneling System—User's Manual"; 2000; pp. 1-16.

* cited by examiner

*Primary Examiner*—Thomas C Barrett
*Assistant Examiner*—Michael J Araj
(74) *Attorney, Agent, or Firm*—Harness, Dickey

(57) ABSTRACT

A method and apparatus for repairing soft tissue through a less invasive procedure. Generally, a single shaft instrument is provided to allow for the drilling of a non-linear path into bone to facilitate tissue repair. An arthroscope can be used to monitor the procedure. Thus, smaller incisions can be made to repair soft tissues.

30 Claims, 5 Drawing Sheets

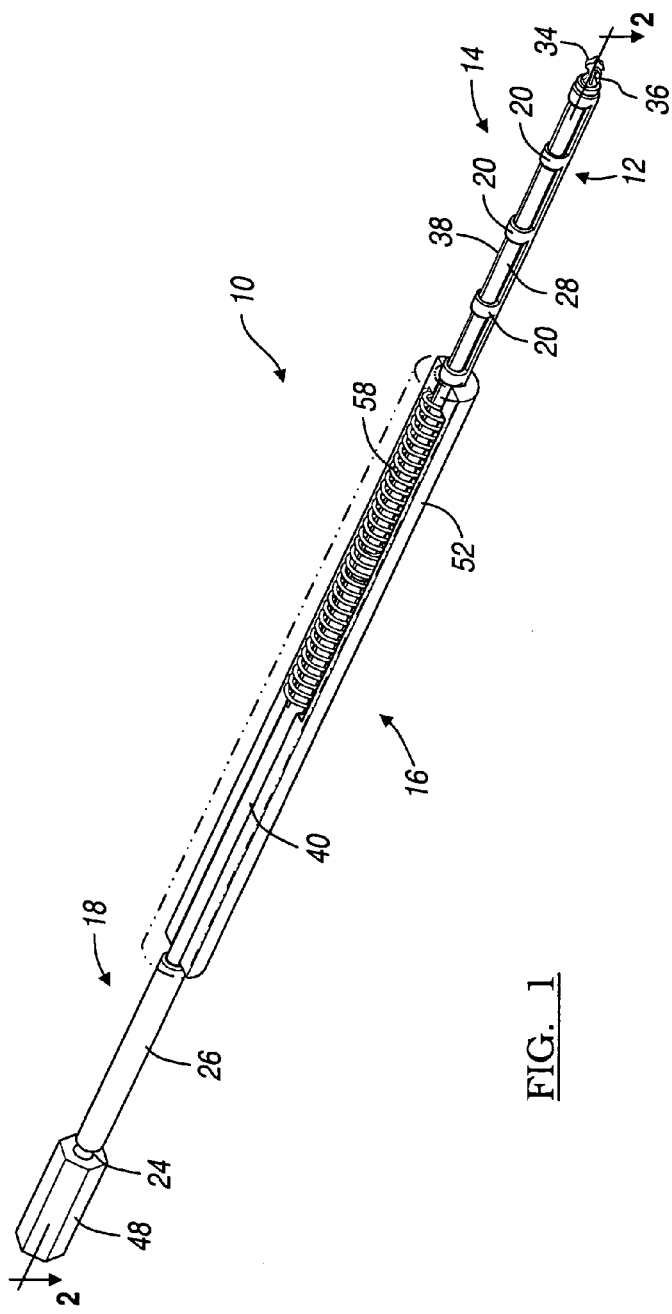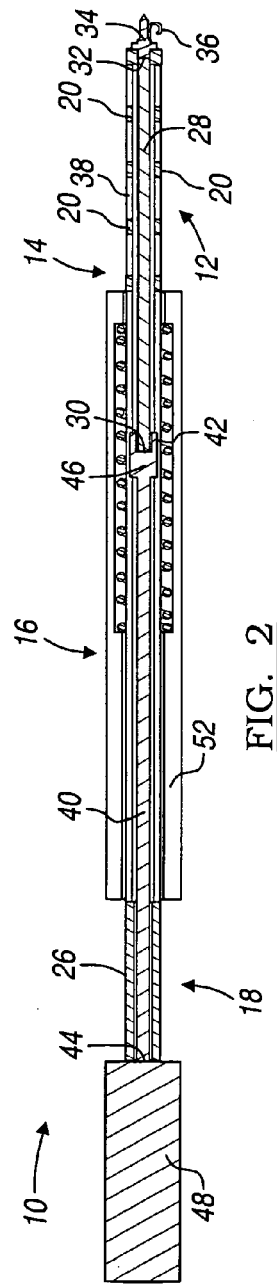

METHOD AND APPARATUS FOR ARTHROSCOPIC TUNNELING

FIELD

The present invention relates generally to orthopedic surgical procedures and instruments, and particularly to methods and apparatuses for arthroscopic tunneling.

BACKGROUND

Various procedures may be performed to repair soft tissue in the body. Generally, it is known to drill a curved path into bone using two cutting ends which meet in the center of the curved path. Then, the soft tissue is secured to the bone with a suture which "wraps around" the soft tissue and bone by passing through the curved tunnel.

This procedure, however, requires at least two incisions and a larger surface area to perform the operation. Each required incision may increase the healing time for the patient. In addition, the use of two cutting ends requires the use of a sizable instrument which reduces the efficiency of the intended repair operation. In particular, a large instrument may be hard to hold and manipulate, making the precise work of soft tissue repair tedious.

Therefore, it is desirable to provide an instrument that allows for a less invasive procedure so that the precise work of the soft tissue repair can occur without substantial trauma to the patient. Particularly, it may be desirable to allow a tunnel to be formed substantially percutaneously and through small incisions.

SUMMARY

A method and apparatus for repairing soft tissue through a less invasive procedure. Generally, a single shaft instrument is provided to allow for the drilling of a non-linear path into bone to facilitate tissue repair. An arthroscope can be used to monitor the procedure. Thus, smaller incisions can be made to repair soft tissues.

An instrument for arthroscopic tunneling includes a housing having a flexible drill shaft disposed therein. The flexible drill shaft is coupled to a drill head for tunneling into a bone. A guiding mechanism coupled to the flexible drill shaft is operable to guide the flexible drill shaft in a selected non-linear cutting path. The selected curved cutting path includes entering at a first position of the bone and exiting at a second position of the bone spaced a distance from the first position of the bone.

An assembly for arthroscopic tunneling includes a housing operable to selectively engage a drill and a flexible rod disposed in the housing. The flexible rod is operable to extend beyond the housing and a flexible drill shaft is coupled to the flexible rod. The flexible drill shaft is further coupled to a drill head for tunneling into a bone. A guiding mechanism is coupled to the flexible rod and is operable to guide the flexible drill shaft in a selected cutting path. The selected cutting path includes forming a non-linear path by entering the bone at a first location on a bone surface and exiting the bone at a second location on the bone surface.

A method of cutting a non-linear tunnel into a bone including positioning a single shaft cutting tool adjacent to the bone at a first location. Next, cutting a non-linear path through the bone so as to cause the single shaft cutting tool to exit the bone structure at a second bone surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an instrument according to various embodiments;

FIG. 2 is a cross-sectional view taken along line 2-2 of FIG. 1; and

DETAILED DESCRIPTION OF VARIOUS EMBODIMENTS

Figure 3:
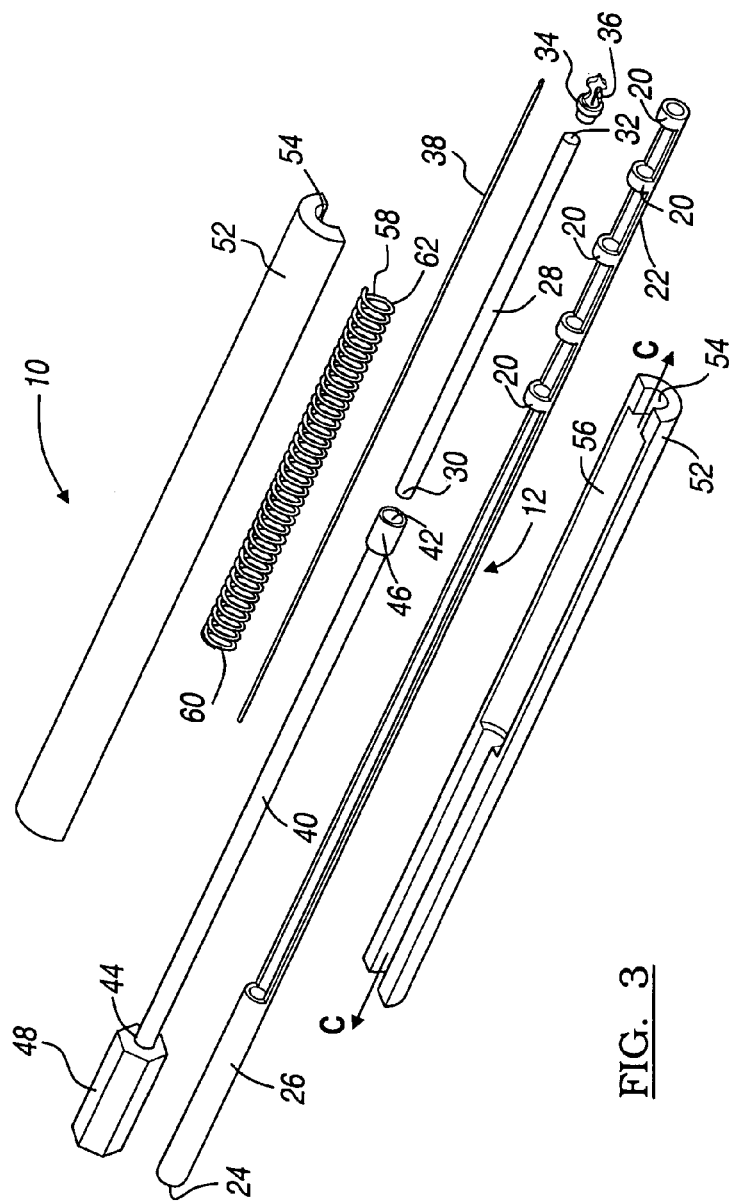
FIG. 3 is an exploded view of the instrument in FIG. 1.

The following description of various embodiments is merely exemplary in nature and is in no way intended to limit the invention, its application, or uses. Although the following description relates generally to soft tissue repair in the shoulder and the formation of a curved tunnel therein, it will be understood that the described instruments and methods may be used for any appropriate procedure. For example, various embodiments may be used to repair soft tissue in the knee. Therefore, it will be understood that the following discussions is not intended to limit the scope of the appended claims.

With reference to FIG. 1, a tunneling device for soft tissue repair 10 is illustrated. The tunneling device 10 may be used to drill into a humerus, as described herein. Those skilled in the art will also understand that the tunneling device 10 may be used to tunnel into other bones as well and may also be used to drill a straight tunnel into a bone. Nevertheless, the tunneling device 10 generally includes a flexible rod 12 for supporting a drilling member 14, a cartridge portion 16 and a positioning member 18.

With continuing reference to FIG. 1 and additional reference to FIGS. 2 and 3, the flexible rod 12 extends the length of the tunneling device 10 to support the drilling member 14 and couples the drilling member 14 to the positioning member 18. More specifically, as best shown in FIG. 3, the flexible rod 12 includes a first plurality of formed loops 20 at a proximal end 22 which couple the drilling member 14 to the flexible rod 12. At a distal end 24 of the flexible rod 12, a second formed loop 26 slideably engages the positioning member 18 so as to allow the movement of the positioning member 18 to guide the drilling member 14, as will be described in more detail below. The flexible rod 12 may be composed of a memory shape alloy, such as NITINOL®. By forming the flexible rod 12 out of a memory shape alloy, the curvature of the flexible rod 12 can be precisely controlled, enabling the curvature of the path formed by the drilling member 14 to be selected prior to use. In particular, it is generally known that a shape memory alloy can be formed into a selected shape or curvature which it will maintain under normal conditions. In this instance, the flexible rod 12 is forced into a straight position in the cartridge portion 16. Thus, upon release from the cartridge portion 16 the flexible rod 12 begins to bend back into its selected curved state which causes the drilling member 14 to curve as well.

With reference now to FIGS. 1 and 2 and continuing reference to FIG. 3, the drilling member 14 includes a flexible drill shaft 28 having a first end 30 coupled to the positioning member 18 and a second end 32 coupled to a drill head 34 and the proximal end 22 of the flexible rod. The flexible drill shaft 28 and drill head 34 can be used to drill into bone as further described herein. The flexible drill shaft 28 may be any appropriate shaft such as that described in commonly owned U.S. Pat. No. 6,267,679 incorporated by reference herein in its entirety. The drill head 34 may be coupled to the flexible drill shaft 28 via crimping, however other known attachment mechanisms may be employed. In addition, the flexible drill shaft 28 and drill head 34 may alternatively be formed as one integral part. The drill head 34 may further include a suture receiver or retriever 36. The suture receiver 36 may be a hook-type, however other configurations may be used.

Figure 4:
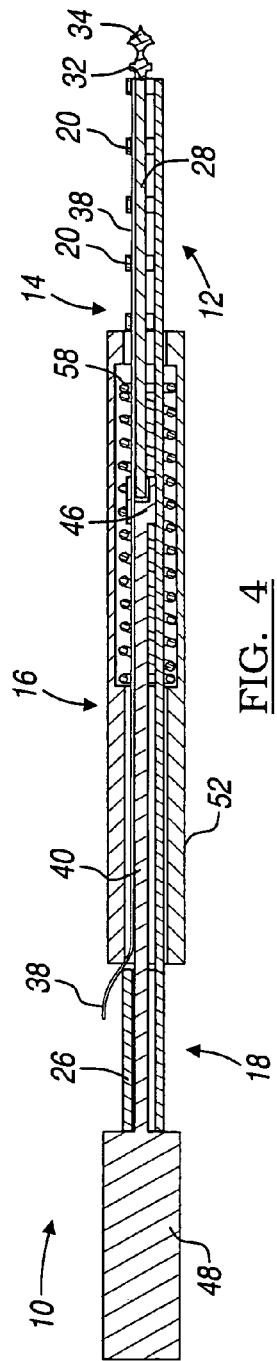
FIG. 4 is a cross-sectional view of various embodiments of FIG. 1 along line 2-2 of FIG. 1.

A flexible member or guide wire 38 may be further coupled to the flexible drill shaft 28 at the second end 32. The guide wire 38 forces or guides the flexible drill shaft 28 into a selected path, such as a curved or non-linear path, as will be further described. In one embodiment, as shown in FIG. 2, the guide wire 38 is coupled to the cartridge portion 16 such that the movement of the positioning member 18 causes the guide wire 38 to pull the flexible drill shaft 28 into a curved path. Specifically, the guide wire 38 has a set length so that upon movement of the positioning member 18, the guide wire 38 must move in a non-linear path as further described herein. It will also be understood that the guide wire 38 is used to decrease the rate of forward movement of the flexible drill shaft 28 in the cartridge portion 16, and that any other suitable device may be employed. Alternatively, the guide wire 38 may be extended through the cartridge portion 16 such that the guide wire 38 may be manually manipulated as shown in FIG. 4.

Figure 5:
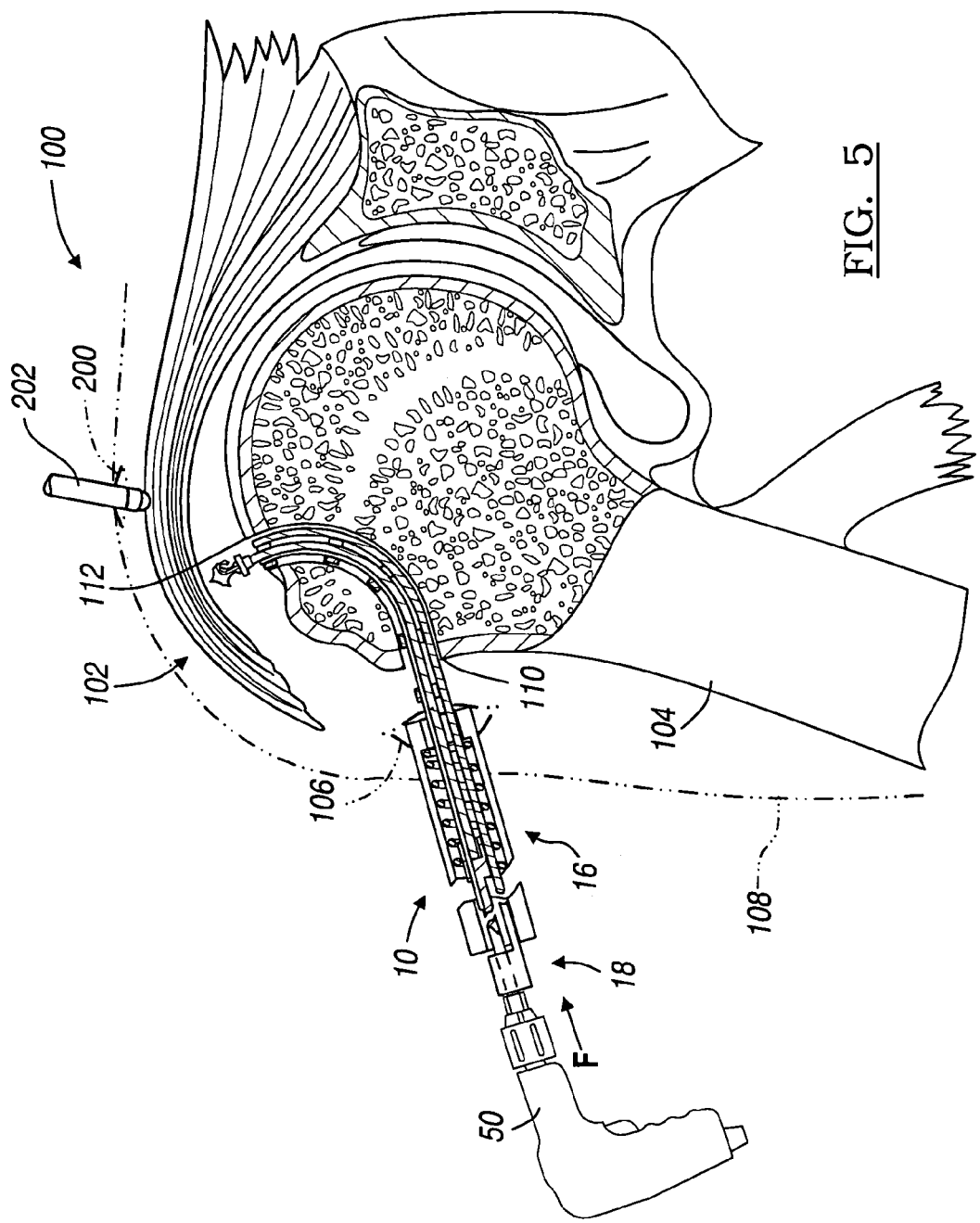
FIG. 5 is an environmental view of a use of the instrument according to various embodiments.

The flexible drill shaft 28 and drill head 34 are also coupled to the positioning member 18. The positioning member 18 includes a cylindrical rod 40 having a proximal end 42 and a distal end 44. The proximal end 42 of the cylindrical rod 40 has a formed cup 46 for retaining the flexible drill shaft 28 of the drilling member 14 therein. In addition, a coupler 48 may be attached to the distal end 44 of the cylindrical rod 40 to couple the cylindrical rod 40 to a drill motor 50 as best shown in FIG. 5. The drill 50 provides the torque required for the drilling member 14 to cut into the bone. The cylindrical rod 40 and the coupler 48 may be formed from any appropriate material, and may be made of the same or different materials. Alternatively, the cylindrical rod 40 and coupler 48 may be integrally formed. Referring back to FIGS. 1, 2 and 3, the cylindrical rod 40 is slideably engaged with the cartridge portion 16 to enable the extension of the flexible drill shaft 28 of the drilling member 14 outside of the cartridge portion 16.

The cartridge portion 16 may generally be of a clamshell configuration with two interlocking halves 52 defining a through bore 54 therein. The through bore 54 is generally formed along a centerline C. The through bore 54 is configured for receipt of the cylindrical rod 40 of the positioning member 18 and the flexible rod 12 with the flexible drill shaft 28 of the drilling member 14 attached thereto. In addition, the through bore 54 defines a chamber 56 which may be used to retain a spring 58. The spring 58 has a first end 60 and a second end 62. The first end 60 of the spring 58 encases the cylindrical rod 40 of the positioning system 18 while the second end 62 encases the flexible drill shaft 28 of the drilling member 14.

The spring 58 may assist in guiding the drill shaft 28. The guide wire 38 may be coupled to the first end 60 of the spring 58 in order to provide automatic tensioning of the guide wire 38 during operation of the drilling member 14, as described herein. In various embodiments shown in FIG. 4, the guide wire 38 is positioned under the spring 58 and is not coupled to the spring 58 to allow manual manipulation.

Figure 6:
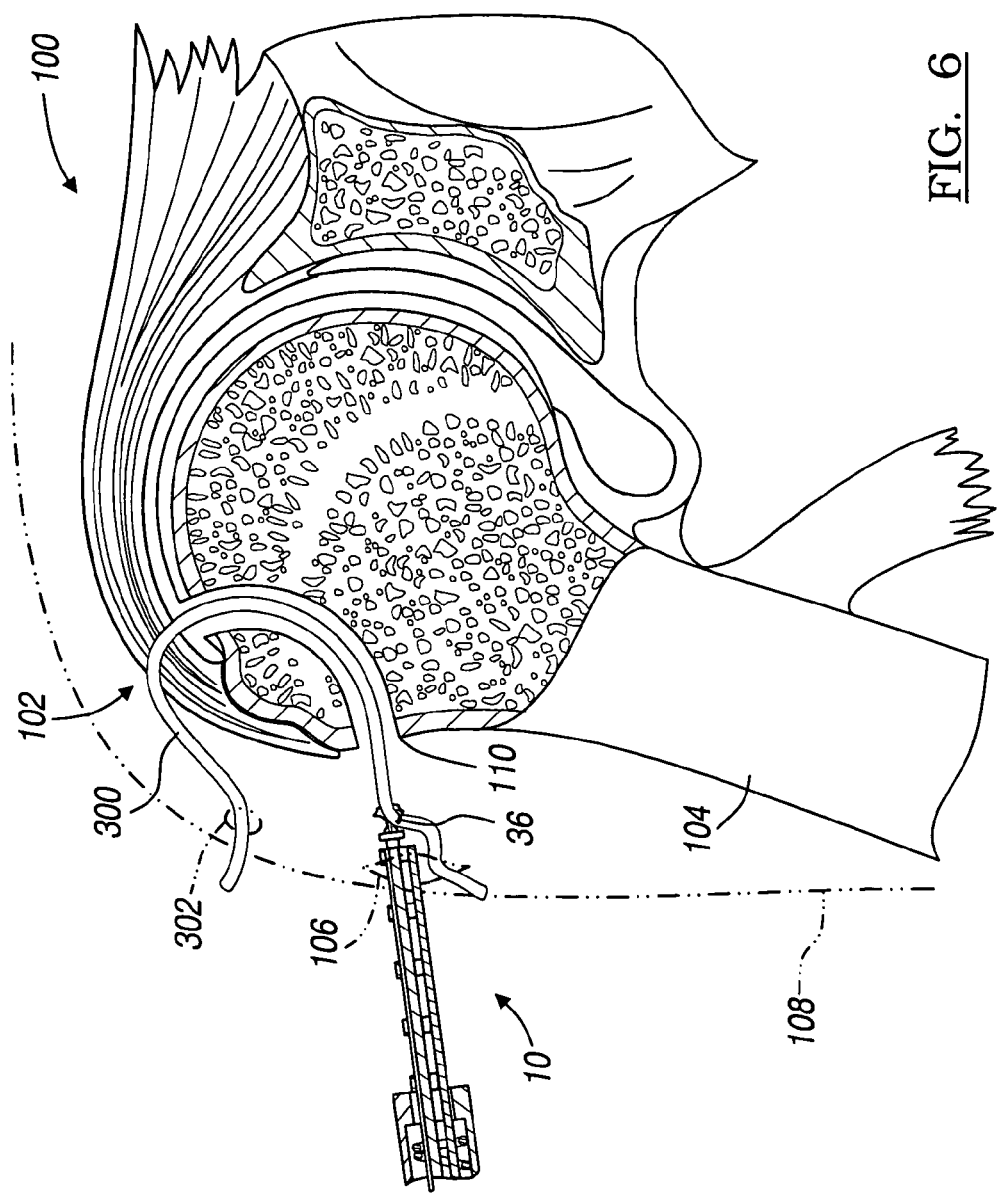
FIG. 6 is an environmental view illustrating the intermediary step in the procedure of FIG. 5.
Figure 7:
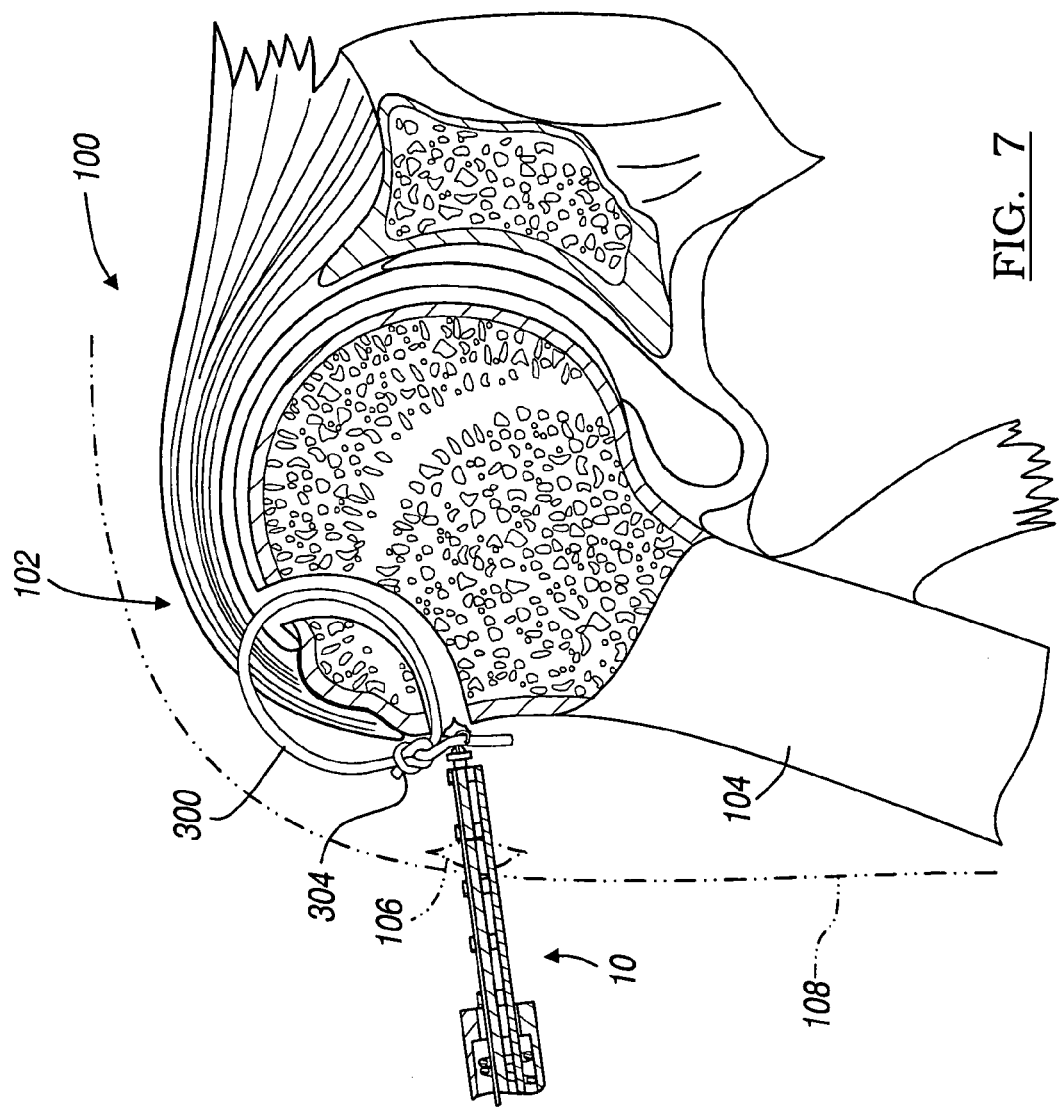
FIG. 7 is an environmental view of the completed procedure of FIG. 5.

With reference now to FIGS. 1, 2 and 3 and with particular reference to FIGS. 5, 6 and 7, a shoulder 100 is shown undergoing a soft tissue reattachment 102 according to various embodiments of the present invention. More specifically, the tunneling device 10 has drilled a curved path through a humerus 104. In order to drill the curved path, an incision 106 may be made in the tissue 108 surrounding the shoulder 100. Next, the tunneling device 10 is placed near to a first bone or position surface 110 and the drill member 12 is activated to begin the tunneling through the humerus 104. The flexible drill shaft 28 begins by cutting a first straight or selected path into the first bone position 110 of the humerus 104.

According to various embodiments, as shown in FIGS. 1, 2 and 3, when a curved path is desired, the operator applies a force F on the cylindrical rod 40, causing the flexible rod 12 and flexible drill shaft 28 to bend due to the interaction of the spring 58 with the guide wire 38 coupled to the flexible drill shaft 28. More specifically, the force F may cause the flexible rod 12 to extend further beyond the cartridge portion 16, but the flexible rod 12 is prevented from moving further downward due to tension applied to the first end 30 of the flexible drill shaft 28 by the guide wire 38. Thus, the flexible rod 12 must curve along the selected path when the force F is applied. As the operator applies more force F, the spring 58 compresses, allowing for continued non-linear travel as shown in FIG. 5. Specifically, the compression of the spring 58 enables the guide wire 38 to move further along in the direction of the force F and thus the flexible drill shaft 28 can move further in the creation of the curved path. Although the spring 58 is not necessary, it may assist in the operation by reducing stress to the instrument 10. In various embodiments of FIG. 4, the operator may instead pull on the guide wire 38 extending from the cartridge portion 16 to cause the flexible rod 12 to begin the curved path.

Also, a second incision 200 can be made adjacent to the first bone surface 110 for the insertion of an arthroscope 202 as best shown in FIG. 7. The arthroscope 202 enables the operator to monitor the progress of the procedure.

The tunneling device 10 may then exit a second bone surface or position 112 of the humerus 104 as shown in FIG. 5 such that a completed curved path is formed. Next, referring to FIG. 6, a suture 300 can be inserted through a third incision 302, by either a needle or tweezers as generally known in the art. The suture 302 may also be passed through an existing incision, such as through a canula including the arthroscope. The suture 300 is then looped around the suture receiver 36 on the tunneling device 10. Thus, as the tunneling device 10 is removed from the curved path, the suture 300 is pulled back through the curved path. Finally, the suture 300 can then be tied right to the humerus 104 in a knot 304 as shown in FIG. 7. This technique is known as the "tunnel/tie down" technique and maximizes the tissue to bone-compression for optimum healing.

Hence, the tunneling device 10 of the present invention allows for soft tissue repair to be completed using only a single shaft drilling device which enables the operator to engage in tissue repair which optimizes healing and recovery.

In addition, the use of a single shaft instrument reduces the trauma to the patient and reduce the cost of the device. The tunneling device 10 can further be used to secure a suture to the bone after the curved path has been formed. The suture retriever 36 may decrease steps and decrease operation time.

The flexible rod 12 and the guide wire 38 form a guide mechanism, that may be used together or alone. As discussed above, the guide mechanism allows a user to navigate the flexible drill shaft 28 along a selected path. More specifically, the guide mechanism enables the user to steer, direct or manipulate the flexible drill shaft 28 along a selected path which may or may not be defined by a single radius. Thus, the path need not be pre-determined or enforced by a rigid exterior member. Rather, the path may be selected during the procedure depending upon various considerations.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of forming a non-linear tunnel through a bone structure, comprising:
    positioning at least a portion of a flexible single shaft cutting tool through a flexible guide mechanism;
    positioning the flexible single shaft cutting tool adjacent to the bone structure at a first bone location;
    guiding the flexible single shaft cutting tool with the flexible guide mechanism from the first bone location to a second bone location;
    cutting a non-linear path with the flexible single shaft cutting tool through the bone structure from the first bone location to the second bone location so as to cause the flexible single shaft cutting tool to enter the bone structure at the first bone location and exit the bone structure at the second bone location;
    associating a suture engaging hook with the flexible single shaft cutting tool;
    engaging a suture with the suture engaging hook at the second bone location; and
    pulling the suture through the non-linear path from the second bone location to the first bone location to secure the suture to a selected tissue near to the first and second bone location after the non-linear path has been formed.

2. The method of claim 1 further comprising forming the non-linear path in the bone substantially percutaneously.

3. The method of claim 1 wherein the first location and second location are co-planar.

4. The method of claim 1 wherein guiding the flexible single shaft cutting tool with the flexible guide mechanism further comprises:
    directing the flexible single shaft cutting tool in the non-linear path with a strand.

5. The method of claim 1 wherein guiding the flexible single shaft cutting tool with the flexible guide mechanism further comprises:
    directing the flexible single shaft cutting tool in the non-linear path with a rod formed of a memory-shape alloy.

6. The method of claim 1 further comprising:
    viewing the cutting of the non-linear path with an arthroscope.

7. The method of claim 1, wherein cutting the non-linear path further comprises:
    extending a flexible single shaft cutting tool having a continuous drill shaft through the bone structure from the first bone location to the second bone location.

8. The method of claim 1, further comprising:
    flexing the single shaft cutting tool from a first configuration to a second configuration.

9. The method of claim 1, wherein the non-linear path is defined by more than a single radius.

10. The method of claim 1, wherein the non-linear path is a non-predetermined path.

11. A method of forming a non-linear tunnel through a bone structure, comprising:
    interconnecting a flexible drill shaft and a drill head;
    forming a small incision in a tissue near the bone structure;
    passing the drill head with the flexible drill shaft percutaneously through the small incision;
    drilling into the bone structure with the drill head at an entering position;
    guiding the drill head with the flexible drill shaft with a guide mechanism along a selected non-linear cutting path within the bone structure by:
        positioning at least a portion of the flexible drill shaft through a flexible rod;
        connecting a flexible member to a portion of the flexible drill shaft;
        sliding a handle to tension the flexible member to assist in directing the flexible drill shaft along the selected non-linear path; and
    forming the selected non-linear cutting path with the drill head between the entering position into the bone structure and an exiting position out of the bone structure that is spaced a distance from the entering position in the bone structure.

12. The method of claim 11 further comprising:
    providing a suture near the exiting position;
    moving the drill head and the flexible drill shaft;
    engaging the suture with a suture mechanism near the drill head; and
    pulling the suture from the exiting position to the entering position with the suture mechanism.

13. The method of claim 11 wherein the guide mechanism further includes:
    the flexible rod at least partially enclosing at least a portion of the flexible drill shaft and having a proximal end and a distal end, the flexible drill shaft coupled to the flexible rod at the proximal end; and
    the flexible member interconnected with a distal end of the flexible drill shaft.

14. The method of claim 13 wherein the flexible rod is made from a shape memory alloy.

15. The method of claim 11, further comprising:
    selecting a first path that is linear or non-linear of the drill head;
    selecting a second path that is linear or non-linear of the drill head;
    wherein sliding the handle to tension the flexible member moves the flexible member to engage the drill head or the flexible drill shaft to move the drill head from the selected first path to the selected second path during forming the selected non-linear cutting path.

16. The method of claim 11, wherein guiding the drill head includes:
    passing at least one of the flexible drill shaft, the drill head, or combinations thereof through a flexible rod, moving the flexible rod to engage and direct at least one of the flexible drill shaft, the drill head, or combinations thereof;
    wherein forming the selected non-linear cutting path includes directing at least one of the flexible drill shaft, the drill head, or combinations along a first path and directing at least one of the flexible drill shaft, the drill head, or combinations along a second path.

17. The method of claim 16 wherein forming the selected non-linear path includes forming the first path linearly and the second path non-linearly while forming the selected non-linear cutting path.

18. The method of claim 11, wherein forming the small incision near the bone structure includes forming the small incision near a humeral head of a humerus.

19. The method of claim 18, further comprising:
engaging a select tissue with the suture;
moving a suture through the tunnel formed in the humerus after the tunnel is formed;
tying the suture to the humerus; and
compressing a tissue to the humerus.

20. The method of claim 11, further comprising:
flexing the flexible member from a first configuration to a second configuration with the handle.

21. A method of forming a non-linear tunnel through a bone structure, comprising:
identifying the bone structure as at least one of a humerus, humeral head, glenoid, or combinations thereof;
forming an incision in tissue relative to the identified bone structure;
drilling into the identified bone structure with a drill head associated with a flexible drill shaft;
guiding the drill head and flexible drill shaft with a flexible guide mechanism through an entry position and through the identified bone structure in a first direction, by:
engaging a flexible rod with a housing with the flexible drill shaft;
coupling the flexible drill shaft to the flexible rod at a proximal end;
engaging a handle with a distal end of the flexible rod and the housing;
manipulating the handle to direct the flexible drill shaft along a non-predetermined path;
forming a tunnel with the drill head along the non-predetermined path;
exiting the identified bone structure at an exit position with the drill head;
moving a suture engaging member near the drill head through the formed tunnel;
pulling a suture through the formed tunnel in a second direction to pull the suture from the exit position to the entry position; and
engaging the identified bone structure with the suture.

22. The method of claim 21, wherein the non-predetermined path includes a first path and a second path, in which the first path is formed along at least one of a curved path and straight path and the second path is formed along at least one of a straight path and a curved path;
wherein the first path and the second path are formed by changing a direction of the drill head.

23. The method of claim 21, further comprising:
passing the suture through a soft-tissue near the humeral head; and
compressing the soft-tissue to the identified bone structure with the suture.

24. The method of claim 21, further comprising:
positioning an arthroscope near at least one of the entry position, the exit position, or combinations thereof.

25. The method of claim 21, further comprising:
interconnecting a flexible member to the flexible drill shaft; and
sliding the handle to cause tension in the flexible member to direct the flexible drill shaft along the first and second path while forming the tunnel;
wherein guiding the drill head includes changing a direction of the drill head after beginning forming the tunnel.

26. The method of claim 21, further comprising:
coupling a flexible member to the flexible drill shaft;
extending the flexible member through the housing; and
manipulating the flexible member manually to direct the flexible drill shaft along the first and second path.

27. The method of claim 21, wherein the entry position is near at least one of a lateral side of the humerus, a superior side of the humeral head, or combinations thereof; and
the exit position is at least one of the other of the lateral side of the humerus, the superior side of the humeral head, or combinations thereof.

28. The method of claim 27, further comprising:
passing the suture through a soft-tissue near the humeral head; and
compressing the soft-tissue to the superior side of the humeral head with the suture.

29. The method of claim 21, wherein pulling the suture through the formed tunnel further comprises:
pulling the suture through the formed tunnel in the second direction after the tunnel is formed.

30. The method of claim 21, wherein the second direction is opposite the first direction.

* * * * *

UNITED STATES PATENT AND TRADEMARK OFFICE
CERTIFICATE OF CORRECTION

| | |
|---|---|
| PATENT NO. | : 7,604,636 B1 |
| APPLICATION NO. | : 10/828494 |
| DATED | : October 20, 2009 |
| INVENTOR(S) | : Walters et al. |

It is certified that error appears in the above-identified patent and that said Letters Patent is hereby corrected as shown below:

Column 5, Line 63, "cuffing" should be -- cutting --

Signed and Sealed this

Third Day of August, 2010

David J. Kappos
*Director of the United States Patent and Trademark Office*